United States Patent
Hadley et al.

(10) Patent No.: US 6,245,778 B1
(45) Date of Patent: Jun. 12, 2001

(54) 1,6-NAPHTHYRIDINE ANTI-CONVULSANTS

(75) Inventors: Michael Stewart Hadley, Sawbridgeworth; John David Harling, Harlow; Frank Peter Harrington, Sawbridgeworth; Mervyn Thompson, Harlow; Robert William Ward, Great Dunmow, all of (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/424,399

(22) PCT Filed: May 29, 1998

(86) PCT No.: PCT/GB98/01575

§ 371 Date: Nov. 23, 1999

§ 102(e) Date: Nov. 23, 1999

(87) PCT Pub. No.: WO98/54184

PCT Pub. Date: Dec. 3, 1998

(30) Foreign Application Priority Data

May 30, 1997 (GB) .................................................. 9711257

(51) Int. Cl.$^7$ .................... A61K 31/4375; C07D 471/04; A61P 25/08
(52) U.S. Cl. ............................................ 514/300; 546/122
(58) Field of Search .............................. 514/300; 546/122

(56) References Cited

U.S. PATENT DOCUMENTS 5,378,848 * 1/1995 Takada .................................... 546/82

FOREIGN PATENT DOCUMENTS

| 0 172 083 | 2/1986 | (EP) . |
| 0 234 971 | 9/1987 | (EP) . |
| 0 556 008 | 8/1993 | (EP) . |
| 0 588 500 | 3/1994 | (EP) . |
| WO 97/34894 | 9/1997 | (WO) . |

\* cited by examiner

Primary Examiner—Evelyn Mei Huang
(74) Attorney, Agent, or Firm—Linda E. Hall; William T. King; Charles M. Kinzig

(57) ABSTRACT

Compounds of formula (I) and pharmaceutically acceptable salts thereof:

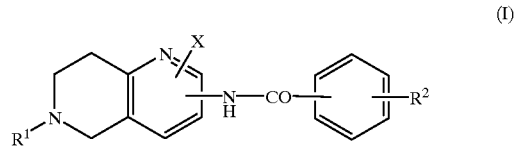

(I)

where $R^1$ is hydrogen, $C_{1-6}$ alkyl optionally substituted by hydroxy or $C_{1-4}$alkoxy, or $C_{1-6}$ alkylphenyl;

$R^2$ is hydrogen or up to three substituents selected from halogen, $NO_2$, CN, $N_3$, $C_{1-6}$ alkylO-, $C_{1-6}$ alkylS-, $C_{1-6}$ alkyl, $C_{3-6}$cycloalkyl, $C_{3-6}$cycloalkyl-$C_{1-4}$alkyl-, $C_{1-6}$alkenyl, $C_{1-6}$alkynyl, $CF_3$, $CF_3O$, $CF_3CO-$, $C_{1-6}$alkylCO-, $C_{3-6}$cycloalkylCO-, $C_{3-6}$cycloalkyl-$C_{1-4}$alkylCO-, phenyl, phenoxy, benzyloxy, benzoyl, phenyl-$C_{1-4}$alkyl-,
or $-NR^3R^4$ where
$R^3$ is hydrogen or $C_{1-4}$ alkyl, and
$R^4$ is hydrogen, $C_{1-4}$alkyl, $-CHO$, $-CO_2C_{1-4}$alkyl or $-COC_{1-4}$alkyl;
or two $R^2$ groups form a saturated carbocyclic ring optionally interrupted by oxygen;
and X is selected from hydrogen, halogen, cyano, alkyl and alkoxy;

are useful in the treatment and prophylaxis of inter alia epilepsy.

7 Claims, No Drawings

1,6-NAPHTHYRIDINE ANTI-CONVULSANTS

This application is the national phase of PCT/GB98/01575 filed May 29, 1998.

This invention relates to novel compounds, to processes for preparing them, and to their use as therapeutic agents.

EP-A-0556008 (Shionogi) discloses condensed imidazopyridine derivatives with psychotropic activity, including the compound 1,6naphthyridine-6(5H)-carboxylic acid, 4-azido-3-[[(1,1-dimethylethoxy) carbonyl]amino]-7,8-dihydro, ethyl ester.

It has now been surprisingly found that carboxamide compounds of formula (I) below possess anti-convulsant activity and are therefore believed to be useful in the treatment and/or prevention of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, amyotrophic lateral sclerosis, ataxias, muscular rigidity (spasticity) and temporomandibular joint dysfunction.

Accordingly, the present invention provides a compound of formula (I) or pharmaceutically acceptable salt thereof:

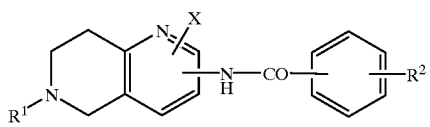

(I)

where
- $R^1$ is hydrogen, $C_{1-6}$alkyl optionally substituted by hydroxy or $C_{1-4}$alkoxy, or $C_{1-6}$alkylphenyl;
- $R^2$ is hydrogen or up to three substituents selected from halogen, $NO_2$, $CN$, $N_3$, $C_{1-6}$ alkylO-, $C_{1-6}$ alkylS-, $C_{1-6}$ alkyl, $C_{3-6}$cycloalkyl, $C_{3-6}$cycloalkyl-$C_{1-4}$alkyl-, $C_{1-6}$alkenyl, $C_{1-6}$alkynyl, $CF_3$, $CF_3O$, $CF_3CO$—, $C_{1-6}$alkylCO-, $C_{3-6}$cycloalkylCO-, $C_{3-6}$cycloalkyl-$C_{1-4}$alkylCO-, phenyl, phenoxy, benzyloxy, benzoyl, phenyl-C 14alkyl-, or —$NR^3R^4$ where
  - $R^3$ is hydrogen or $C_{1-4}$ alkyl, and
  - $R^4$ is hydrogen, $C_{1-4}$alkyl, —CHO, —$CO_2C_{1-4}$alkyl or —$COC_{1-4}$alkyl;
  - or two $R^2$ groups form a saturated carbocyclic ring optionally interrupted by oxygen;
- and X is selected from hydrogen, halogen, cyano, alkyl and alkoxy.

The compounds of this invention are typically naphthyridin-3-yl-benzamides.

In the formula (I), alkyl groups, including alkyl groups that are part of another moiety, may be straight chain or branched. Aromatic rings, especially phenyl groups, (including rings that are part of another moiety), may optionally be substituted with one or more independently selected halogen or $C_{1-6}$ alkyl, $C_{3-6}$ cycloalkyl, $C_{1-6}$ alkoxy or $C_{1-6}$alkylcarbonyl.

Suitable $C_{3-6}$ cycloalkyl groups include cyclopropyl, cyclobutyl, cyclopentyl, and cyclohexyl.

Suitable halo substituents include fluoro, chloro, iodo and bromo.

A suitable group of compounds of formula (I) have
- $R^1$ as hydrogen, methyl or benzyl
- $R^2$ as hydrogen, methoxy, ethoxy, iso-propyloxy, methyl, ethyl, iso-propyl, tert-butyl, pivaloyl, trifluoromethyl, chloro, bromo, or nitro.

Examples of compounds of formula (I) are:
N-(6-methyl-5,6,7,8-tetrahydro[1,6]naphthyridin-3-yl)-3-bromo-4-methoxybenzamide and its monohydrochloride
N-(6-methyl-5,6,7,8-tetrahydro[1,6]naphthyridin-3-yl)-benzamide
N-(6-methyl-5,6,7,8-tetrahydro[1,6]naphthyridin-3-yl)-2-methoxy-4-t-butylbenzamide and its monohydrochloride
N-(6-methyl-5,6,7,8-tetrahydro[1,6]naphthyridin-3-yl)-4-iso-propoxybenzamide and its monohydrochloride
N-(6-methyl-5,6,7,8-tetrahydro[1,6]naphthyridin-3-yl)-4-ethoxybenzamide and its monohydrochloride
N-(6-methyl-5,6,7,8-tetrahydro[1,6]naphthyridin-3-yl)-2-methoxy-5-pivaloylbenzamide and its monohydrochloride
N-(6-methyl-5,6,7,8-tetrahydro[1,6]naphthyridin-3-yl)-3-trifluoromethyl benzarnide and its monohydrochloride
N-(6-benzyl-5,6,7,8-tetrahydro[1,6]naphthyridin-3-yl)-3-bromo-4-methoxybenzamide
N-(6-methyl-5,6,7,8-tetrahydro[1,6]naphthyridin-3-yl)-4-methoxy-3-trifluoromethylbenzamide and its monohydrochloride
N-(6-methyl-5,6,7,8-tetrahydro[1,6]naphthyridin-3-yl)-4-t-butylbenzamide and its monohydrochloride
N-(6-methyl-5,6,7,8-tetrahydro[1,6]naphthyridin-3-yl)-3-bromo-4-ethoxybenzamide and its monohydrochloride
N-(6-methyl-5,6,7,8-tetrahydro[1,6]naphthyridin-3-yl)-3-bromo-4-iso-propyloxybenzatnide and its monohydrochloride
N-(6-Methyl-5,6,7,8-tetrahydro[1,6]naphthyridin-3-yl)-3-chloro-4-methoxybenzamide, hydrochloride
N-(6-Methyl-5,6,7,8-tetrahydro[1,6]naphthyridin-3-yl)-4-ethyl benzamide
N-(6-Methyl-5,6,7,8-tetrahydro[1,6]naphthyridin-3-yl)-4-cyclohexylbenzarnide
N-(6-Methyl-5,6,7,8-tetrahydro[1,6]naphthyridin-3-yl)-4-benzoylbenzamide
N-(6-Methyl-5,6,7,8-tetrahydro[1,6]naphthyridin-3-yl)-2,3-dihydrobenzofuran-5-ylcarboxamide
N-(6-Methyl-5,6,7,8-tetrahydro[1,6]naphthyridin-3-yl)-4-t-butyl-3-trifluoromethylbenzamide
N-(6-Methyl-5,6,7,8-tetrahydro[1,6]naphthyridin-3-yl)-4-iso-propylbenzamide, hydrochloride
N-(6-Methyl-5,6,7,8-tetrahydro[1,6]naphthyridin-3-yl)-4-ethoxy-3-nitrobenzamide hydrochloride
N-(6-Methyl-5,6,7,8-tetrahydro[1,6]naphthyridin-3-yl)-3-bromo-4-t-butylbenzamide, hydrochloride
N-(6-Methyl-5,6,7,8-tetrahydro[1,6]naphthyridin-3-yl)-3-bromo-4-ethylbenzamide, hydrochloride
N-(6-Methyl-5,6,7,8-tetrahydro[1,6]naphthyridin-3-yl)-3-cyano-4-methoxybenzamide, hydrochloride
N-(6-Methyl-5,6,7,8-tetrahydro[1,6]naphthyridin-3-yl)-3-bromo-4-n-propyl-oxybenzamide, hydrochloride
N-(6-Methyl-5,6,7,8-tetrahydro[1,6]naphthyridin-3-yl)-3,5-dichloro-4-methoxybenzamide, hydrochloride N-(6-Methyl-5,6,7,8-tetrahydro[1,6]naphthyridin-3-yl)-3-bromo-4-iso-propylbenzamide, hydrochloride N-(6-Methyl-5,6,7,8-tetrahydro[1,6]naphthyridin-3-yl)-4-n-propyloxy-3-trifluoromethylbenzamide, hydrochloride N-(6-Methyl-5,6,7,8-tetrahydro[1,6]naphthyridin-3-yl)-3-iodo-4-methoxybenzamide hydrochloride N-(6-Methyl-5,6,7,8-tetrahydro[1,6]naphthyridin-3-yl)-4-iso-propyl-3-trifluoromethylbenzamide, hydrochloride N-(6-Methyl-5,6,7,8-tetrahydro[1,6]naphthyridin-3-yl)-3-cyano-4-n-propyloxybenzamide, hydrochloride N-(6-Methyl-5,6,7,8-tetrahydro[1,6]naphthyridin-3-yl)-3-cyano-4-ethoxybenzamide, hydrochloride N-(6-Methyl-5,6,7,8-tetrahydro[1,6]naphthyridin-3-yl)-3-chloro-4-ethoxybenzamide, hydrochloride N-(6-Methyl-5,6,7,8-tetrahydro[1,6]naphthyridin-3-yl)-3-chloro-4-iso-propyloxybenzamide, hydrochloride N-(6-Methyl-5,6,7,8-tetrahydro [1,6]naphthyridin-3-yl)-3-fluoro-4-methoxybenzamide, hydrochloride N-(6-Methyl-5,6,7,8-tetrahydro[1,6]naphthyridin-3-yl]-4-ethyl-3-trifluoromethylbenzamide N-(6-Methyl-5,6,7,8-tetrahydro[1,6]naphthyridin-3-yl)-4-iso-propyloxy-3-trifluoromethylbenzamide, hydrochloride N-(6-Methyl-5,6,7,8-tetrahydro[1,6]naphthyridin-3-yl)-3-iodo-4-methylbenzamide hydrochloride N-(6-Methyl-5,6,7,8-tetrahydro[1,6]naphthyridin-3-yl)-4-azido-3-iodo-benzamide N-(2-Bromo-6-methyl-5,6,7,8-tetrahydro[1,6]naphthyridin-3-yl)-3-bromo-4-ethoxybenzamide N-(2-Bromo-6-methyl-5,6,7,8-tetrahydro[1,6]naphthyridin-3-yl)-4-methoxy-3-trifluoromethylbenzamide, hydrochloride N-(2,6-Dimethyl-5,6,7,8-tetrahydro[1,6]naphthyridin-3-yl)-3-bromo-4-ethoxy-benzamide N-(2,6-Dimethyl-5,6,7,8-tetrahydro[1,6]naphthyridin-3-yl)-4-methoxy-3-trifluoromethylbenzamide N-(2-Cyano-6-methyl-5,6,7,8-tetrahydro[1,6]naphthyridin-3-yl)-4-methoxy-3-trifluoromethylbenzamide N-(2-Chloro-6-methyl-5,6,7,8-tetrahydro[1,6]naphthyridin-3-yl)-3-bromo-4-ethoxybenzamide N-(2-Chloro-6-methyl-5,6,7,8-tetrahydro[1,6]naphthyridin-3-yl)-4-methoxy-3-trifluoromethylbenzamide.

When synthesised, these compounds are often in salt form, typically the hydrochloride or trifluoroacetate, and such salts also form part of this invention. Such salts may be used in preparing pharmaceutically acceptable salts. The compounds and their salts may be obtained as solvates, such as hydrates, and these also form part of this invention.

The above-listed compounds and pharmaceutically acceptable salts thereof, especially the hydrochloride, and pharmaceutically acceptable solvates, especially hydrates, form a preferred aspect of the present invention.

The administration of such compounds to a mammal may be by way of oral, parenteral, sub-lingual, nasal, rectal, topical or transdermal administration.

An amount effective to treat the disorders hereinbefore described depends on the usual factors such as the nature and severity of the disorders being treated and the weight of the mammal. However, a unit dose will normally contain 1 to 1000 mg, suitably 1 to 500 mg, for example an amount in the range of from 2 to 400 mg such as 2, 5, 10, 20, 30, 40, 50, 100, 200, 300 and 400 mg of the active compound. Unit doses will normally be administered once or more than once per day, for example 1, 2, 3, 4, 5 or 6 times a day, more usually 1 to 4 times a day, such that the total daily dose is normally in the range, for a 70 kg adult of 1 to 1000 mg, for example 1 to 500 mg, that is in the range of approximately 0.01 to 15 mg/kg/day, more usually 0.1 to 6 mg/kg/day, for example 1 to 6 mg/kg/day.

It is greatly preferred that the compound of formula (I) is administered in the form of a unit-dose composition, such as a unit dose oral, including sub-lingual, nasal, rectal, topical or parenteral (especially intravenous) composition.

Such compositions are prepared by admixture and are suitably adapted for oral or parenteral administration, and as such may be in the form of tablets, capsules, oral liquid preparations, powders, granules, lozenges, reconstitutable powders, injectable and infusable solutions or suspensions or suppositories. Orally administrable compositions are preferred, in particular shaped oral compositions, since they are more convenient for general use.

Tablets and capsules for oral administration are usually presented in a unit dose, and contain conventional excipients such as binding agents, fillers, diluents, tabletting agents, lubricants, disintegrants, colourants, flavourings, and wetting agents. The tablets may be coated according to well known methods in the art.

Suitable fillers for use include cellulose, mannitol, lactose and other similar agents. Suitable disintegrants include starch, polyvinylpyrrolidone and starch derivatives such as sodium starch glycollate. Suitable lubricants include, for example, magnesium stearate. Suitable pharmaceutically acceptable wetting agents include sodium lauryl sulphate.

These solid oral compositions may be prepared by conventional methods of blending, filling, tabletting or the like. Repeated blending operations may be used to distribute the active agent throughout those compositions employing large quantities of fillers. Such operations are, of course, conventional in the art.

Oral liquid preparations may be in the form of, for example, aqueous or oily suspensions, solutions, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethyl cellulose, aluminnium stearate gel or hydrogenated edible fats, emulsifying agents, for example lecithin, sorbitan monooleate, or acacia; non-aqueous vehicles (which may include edible oils), for example, almond oil, fractionated coconut oil, oily esters such as esters of glycerine, propylene glycol, or ethyl alcohol; preservatives, for example methyl or propyl p-hydroxybenzoate or sorbic acid, and if desired conventional flavouring or colouring agents.

Oral formulations also include conventional sustained release formulations, such as tablets or granules having an enteric coating.

For parenteral administration, fluid unit dose forms are prepared containing the compound and a sterile vehicle. The compound, depending on the vehicle and the concentration, can be either suspended or dissolved. Parenteral solutions are normally prepared by dissolving the compound in a vehicle and filter sterilising before filling into a suitable vial or ampoule and sealing. Advantageously, adjuvants such as a local anaesthetic, preservatives and buffering agents are also dissolved in the vehicle. To enhance the stability, the composition can be frozen after filling into the vial and the water removed under vacuum.

Parenteral suspensions are prepared in substantially the same manner except that the compound is suspended in the vehicle instead of being dissolved and sterilised by exposure to ethylene oxide before suspending in the sterile vehicle. Advantageously, a surfactant or wetting agent is included in the composition to facilitate uniform distribution of the compound of the invention.

As is common practice, the compositions will usually be accompanied by written or printed directions for use in the medical treatment concerned.

Accordingly, in a further aspect, the present invention provides a pharmaceutical composition for use in the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, ataxias, muscular rigidity (spasticity), amyotrophic lateral sclerosis and temporomandibular joint dysfunction, which comprises a compound of formula (I), or a pharmaceutically acceptable salt or solvate thereof, and a pharmaceutically acceptable carrier.

The present invention also provides a method of treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, ataxias, muscular rigidity (spasticity), amyotrophic lateral sclerosis and temporomandibular joint dysfunction, comprising administering to the sufferer in need thereof an effective or prophylactic amount of a compound of formula (I), or a pharmaceutically acceptable salt or solvate thereof.

In a further aspect the invention provides the use of a compound of formula (I), or a pharmaceutically acceptable salt or solvate thereof, for the manufacture of a medicament for the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, ataxias, muscular rigidity (spasticity), amyotrophic lateral sclerosis and temporomandibular joint dysfunction.

In a further aspect the invention provides the use of a compound of formula (I), or a pharmaceutically acceptable salt or solvate, thereof as a therapeutic agent, in particular for the treatment and/or prophylaxis of anxiety, mania, depression, panic disorders and/or aggression, disorders associated with a subarachnoid haemorrhage or neural shock, the effects associated with withdrawal from substances of abuse such as cocaine, nicotine, alcohol and benzodiazepines, disorders treatable and/or preventable with anti-convulsive agents, such as epilepsy including post-traumatic epilepsy, Parkinson's disease, psychosis, migraine, cerebral ischaemia, Alzheimer's disease and other degenerative diseases such as Huntingdon's chorea, schizophrenia, obsessive compulsive disorders (OCD), neurological deficits associated with AIDS, sleep disorders (including circadian rhythm disorders, insomnia & narcolepsy), tics (e.g. Giles de la Tourette's syndrome), traumatic brain injury, tinnitus, neuralgia, especially trigeminal neuralgia, neuropathic pain, dental pain, cancer pain, inappropriate neuronal activity resulting in neurodysthesias in diseases such as diabetes, MS and motor neurone disease, ataxias, muscular rigidity (spasticity) and temporomandibular joint dysfunction.

Another aspect of the invention provides a process for the preparation of compounds of formula (I), which comprises reacting a compound of formula (II)

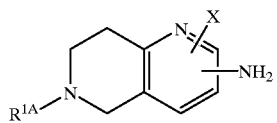

(II)

where $R^{1A}$ is $R^1$ as defined for formula (I) or a group convertible to $R^1$ with a compound of formula (III)

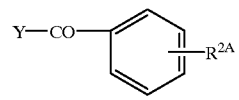

(III)

where Y is Cl or OH, and $R^{2A}$ is $R^2$ as defined for formula (I) or a group or groups convertible to $R^2$,
and where required converting a $R^{1A}$ or $R^{2A}$ group to a $R^1$ or $R^2$ group, converting one X, $R^1$ or $R^2$ group to another X, $R^1$ or $R^2$ group, converting a salt product to the free base or another pharmaceutically acceptable salt, or converting a free base product to a pharmaceutically acceptable salt.

Reaction of a compound of formula (HII) which is a benzoyl chloride derivative (Y═Cl) will lead directly to the hydrochloride salt. Suitable solvents include tetrahydrofuran and ethyl acetate. When the compound of formula (III) is a benzoic acid derivative (Y═OH), conventional conditions for condensation of aromatic acids with amines may be used, for example reacting the components in a mixture of (dimethylaminopropyl)-ethyl-carbodiimide/ hydroxybenzotriazole in a suitable solvent, such as dimethyl formamide.

Conversions of an $R^{1A}$ or $R^{2A}$ group to a $R^1$ or $R^2$ group typically arise when a protecting group is needed during the above coupling reaction or during the preparation of the reactants by the procedures described below. Interconversion of one X, $R^1$ or $R^2$ group to another typically arises when one compound of formula (I) is used as the immediate precursor of another compound of formula (I), or when it is easier to introduce a more complex or reactive substituent at the end of a synthetic sequence.

Compounds of formula (II) may be prepared starting from a compound of formula (IV), that is a dinitro-1-methyl-2-pyridone

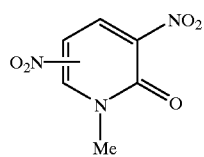

(IV)

by reaction with a compound of formula (V)

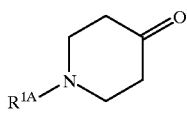

(V)

in a solution of ammonia in a suitable solvent such as methanol, to obtain a compound of formula (VI) using a procedure similar to that of S. Takada et al, *J. Med. Chem*, 1996, 39, 2844.

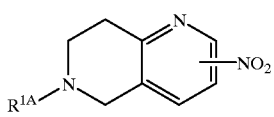

(VI)

Compounds of formula (VI) may be converted to compounds of formula (II) wherein X is hydrogen by hydrogenation or reduction of the nitro group. For example, a compound of formula (VI) may be hydrogenated by treatment with hydrogen in a suitable solvent such as methanol in the presence of a palladium/carbon catalyst. Alternatively, a compound of formula (VI) may be reduced with stannous chloride in concentrated hydrochloric acid in a suitable solvent such as ethanol.

Compounds of formula (IV) may be prepared using the procedure of E. Matsumura, M. Ariga and Y. Tohda, Bull. Chem. Soc. Japan, 52 (8), 2413–2419 (1979).

Compounds of formula (II) wherein X is hydrogen can be converted to compounds wherein X is other using methods known in the art and described hereinbelow in the Descriptions.

Compounds of formula (III) may be prepared by further substitution of commercially available benzoic acid derivatives using conventional procedures, or by oxidation of corresponding substituted benzyl alcohols. Alternatively benzoic acids can be prepared from correspondingly substituted phenols, for example by formation of the acetate, coversion to an acetophenone and then to the desired acid.

The preparation of compounds of formula (II) is illustrated by the following Descriptions; the preparation of compounds of formula (III) is illustrated by the following Preparations; the preparation of compounds of this invention is illustrated by the following Examples. The utility of compounds of this invention is shown by the Pharmacological Data that follow the Examples.

Description 1

6-Benzyl-3-nitro-5,6,7,8-tetrahydro[1,6]naphthyridine 3,5-Dinitro-1-methyl-2-pyridone (1.99 g; 10 mmol) [prepared according to E. Matsumura, M. Ariga and Y. Tohda, Bull. Chem. Soc. Japan, 1979, 52, 2413 ] was added to a solution of ammonia in methanol (1.1M; 100 ml; 110 mmol) and then treated with 1-benzyl-4-piperidone (2.27 g; 12 mmol). The resulting mixture was heated at 60° C. for 5 h, cooled to room temperature and evaporated to dryness in vacuo. The residue was purified by chromatography through $SiO_2$ eluting with 50% ethyl acetate/60–80° pet. ether to give the title compound (2.5 g; 93%). Recrystallisation from ethyl acetate –60–80° petroleum ether gave the title compound as a pale yellow, microcrystalline solid, mp 108° C.

$^1$H NMR (250MHz; $CDCl_3$) δ: 3.03 (2H, t, J=6 Hz), 3.28 (2H, t, J=6 Hz), 3.83 and 3.87 (each 2H, 2s), 7.38-7.49 (5H, m), 8.21 (1H, d, J=2 Hz), 9.33 (1H, d, J=2 Hz);

$^m/_z$: 270.122997; $C_{15}H_{16}N_3O_2$ requires 270.122997. Found: C, 66.75; H, 5.48; N, 15.61%. $C_{15}H_{15}N_3O_2$ requires: C, 66.84; H, 5.56; N, 15.60%.

Description 2

3-Amino-6-benzyl-5,6,7,8-tetrahydro[1,6]naphthyridine

6-Benzyl-3-nitro-5,6,7,8-tetrahydro-[1,6]-naphthyridine (790 mg; 2.93 mmol) was dissolved in ethanol (100 ml), the solution heated at 50° C. and treated with a solution of stannous chloride dihydrate (2.65 g; 11.73 mmol) in conc. hydrochloric acid (10 ml). After 10 min, the reaction mixture was concentrated under reduced pressure, neutralised by addition of 2M aqueous sodium hydroxide and extracted with DCM. The extracts were combined, washed with water, saturated brine, dried ($MgSO_4$) and evaporated to dryness in vacuo. The brown residue was dissolved in methanol and $SiO_2$ added. The volatiles were removed under reduced pressure and the dried $SiO_2$ placed on the top of a silica column and subjected to chromatography, eluting with ethanol in ethyl acetate (0-->20%) ethanol gradient. The title compound was obtained as a white powder (275 mg; 39%).

$^1$H NMR (250MHz, $(CD_3)_2SO$) δ: 2.33 (4H, br m), 3.25 (2H, s), 3.45 (2H, br s), 4.84 (2H, br s, exchangeable), 6.37 (1H, br s), 7.11–7.22 (5H, m), 7.56 (1H, br s)

$^m/_z$ Found: 240.150073. $C_{15}H_{18}N_3$ requires 240.15837.

Description 3

6-Methyl-3-nitro-5,6,7,8-tetrahydro[1,6]naphthyridine 3,5-Dinitro-1-methyl-2-pyridone (5.97 g; 30 mmol) was treated with 1.22M ammonia in methanol (300 ml) then 1-methyl-4-piperidone (3.73 g, 33 mmol) and the mixture heated at 60° for 5 h, then allowed to stand at ambient temp for 72 h. Evaporation in vacuo gave an orange/red residue which was triturated in dichloromethane and diethyl ether, collected by filtration, washed with diethyl ether and dried in air. Chromatography through silica gel, eluting with ethyl acetate, gave the title compound as a red solid (3.4 g, 59%).

$^1$H NMR (250MHz; $CDCl_3$): δ: 2.53 (3H, s), 2.85 (2H, t, J=6 Hz), 3.18 (2H, t, J=6 Hz), 3.69 (2H, s), 8.14 (1H, d, J=2 Hz), 9.23 (1H, d, J=2 Hz);

$^m/_z$ (API): 192.18 (M–H); 194.09 (M+H)$^+$

Description 4

3-Amino-6-methyl-5,6,7,8-tetrahydro[1,6]naphthyridine

6-Methyl-3-nitro-5,6,7,8-tetrahydro[1,6]naphthyridine (2.72 g, 1.41 mmol) was dissolved in methanol (100 ml) and treated with 10% palladium on carbon (1.0 g). The mixture was hydrogenated for 2 h. The catalyst was removed by filtration through Celite, the filter bed washed with methanol and the filtrate evaporated to dryness under reduced pressure to give a yellow solid, which was triturated under diethyl ether and the solids collected by filtration, washed with diethyl ether and dried in vacuo (1.89 g, 83%)

$^1$H NMR (250MHz, CDCl$_3$) $\delta_H$: 2.46 (3H, s), 2.75 (2H, t, J=6 Hz), 2.95 (2H, t, J=6 Hz), 3.50 (2H, s), 3.56 (2H, br s, exchangeable), 6.65 (1H, d, J=2 Hz), 7.92 (1H, d, J=2 Hz); $^m/_z$ (API): 164 (M+H)$^+$ Description 5
3-Amino-2-chloro-6-methyl-5,6,7,8-tetrahydro[1,6] naphthyridine 3-Amino-6-methyl-5,6,7,8-tetrahydro[1,6]naphthyridine D4 (900 mg, 5.52 mmol) was dissolved in acetic acid (50 ml) before being treated portionwise with N-chlorosuccinimide (1.11 g, 8.28 mmol) 20 min. The reaction mixture was stirred overnight at room temperature under argon. The reaction mixture was diluted with water (125 ml), basified to pH10 with solid K$_2$CO$_3$ and extracted with dichloromethane (×2). The combined organic extracts were washed with sodium bicarbonate, dried (MgSO$_4$) and evaporation in vacuo gave a crude black solid. Flash chromatography using dichloromethane (10% MeOH) gave the title compound as a pale orange solid.

$^1$H NMR (CDCl$_3$) $\delta$: 2.46 (3H, s), 2.73 (2H, t), 2.92 (2H, t), 3.49 (2H, s), 3.91 (1H, s), 6.72 (1H, s).

Description 6
3-Amino-2-bromo-6-methyl-5,6,7,8-tetrahydro[1,6] naphthyridine

D4 (978 mg, 6 mmol) was dissolved in acetic acid (10 ml) containing 2M sulphuric acid (2 ml). Bromine (0.31 ml, 6 mmol) was added dropwise with stirring over a period of approximately 25 min. After 2 h, the precipitated solid was removed by filtration and washed with ether to give a pale yellow solid which was dissolved in water. The solution was basified with 2M NaOH and extracted with ethyl acetate. The combined extracts were washed with brine, dried (MgSO$_4$) and evaporation in vacuo gave the crude product as a pale yellow solid (444 mg). The above filtrate from the reaction mixture was concentrated by evaporation in vacuo, diluted with water and made basic with 2M sodium hydroxide. The mixture was extracted with dichloromethane and the extract dried (MgSO$_4$) and evaporated to give a crude brown solid which was purified by chromatography on silica gel eluting with dichloromethane:methanol:aq. ammonia (0.880) (ratio 19:1:0.1). The title compound was obtained as a white solid (248 mg).

$^1$H NMR (250MHz, CDCl$_3$) $\delta$: 2.45 (3H, s), 2.72 (2H, t, J=6 Hz), 2.93 (2H, t, J=6 Hz), 3.46 (2H, s), 3.94 (2H, brs), 6.68 (1H, s).

Description 7
3-Amino-2,6-dimethyl-5,6,7,8-tetrahydro[1,6] naphthyridine

D6 (250 mg, 1.03 mmole) was dissolved in DMF (4 ml) and bis triphenylphosphine palladium (II) chloride (36 mg) and lithium chloride (130 mg) added. A solution of tetramethyltin (190 mg) in DMF (1 ml) was added and the mixture heated at 100° C. under argon for 36 h. A further portion (180 mg) of tetramethyltin and a further portion of palladium catalyst (15 mg) were added and heating contained for a further 24 h. The reaction mixture was evaporated to dryness and chromatographed on silica gel eluting with dichloromethane:methanol:aq ammonia (0.880) (ratio 19:2:0.1). The title compound was obtained as a pale yellow solid (147 mg).

$_1$H NMR (250MHz, d$_6$ acetone) $\delta$: 2.12 (3H, s), 2.30 (3H, s), 2.68 (4H, s), 3.40 (2H, s), 4.28 (ca 2H, br), 6.51 (1H, s); m/z (API$^+$): 178 (MH$^+$, 100%).

Preparation 1
4-iso-Propyloxy-3-trifluoromethylbenzoic acid

Methyl 3-bromo-4-iso-propyloxybenzoate (828 mg; 3.03 mmol) was dissolved in DMF (25 ml) and treated with potassium trifluoroacetate (922 mg; 6.06 mmol), copper (I) iodide (1.15 g; 6.06 mmol) and toluene (50 ml). The resulting mixture was heated at reflux for 1.5 h under Dean and Stark conditions with removal of ca 50 ml of distillate. The resulting mixture was heated at reflux for 18 h then cooled to room temperature, before being poured into a mixture of Et$_2$O (100 ml) and HO (100 ml). The two-phase mixture was stirred at room temperature for 0.5 h then filtered through Celite. The two phases in the filtrate were separated, the aq. phase further extracted with Et$_2$O (50 ml) and the organic extracts combined, washed with saturated, aq. Na$_2$S$_2$O$_3$, H$_2$O, saturated brine, dried (MgSO$_4$) and evaporated to dryness under reduced pressure to give a brown oil. This brown oil was dissolved in MeOH (ca 20 ml) and treated with 2M aq. sodium hydroxide solution (2 ml; 4 mmol) and the resulting solution heated at reflux for 3h. The volatiles were removed under reduced pressure and the residue partitioned between EtOAc and H$_2$O. The phases were separated, the aq. phase acidified to pH1 with 2M hydrochloric acid in the presence of EtOAc and the phases separated. The aq. phase was further extracted with EtOAc, the extracts combined, washed with H$_2$O, saturated brine, dried (MgSO$_4$) and evaporated to dryness underreduced pressure to give the title compound as a white solid. (671 mg; 89%).

$_1$H NMR (250MHz; (CD$_3$)$_2$CO) $\delta$:1.02 (6H, d, J=6 Hz), 4.53–4.63 (1H, m), 7.01 (1H, , J=9 Hz), 7.85–7.88 (2H, m); $^m/_z$ (API$^-$): 205.0 [M–Pr$_i$].

Preparation 2
4-Ethyl-3-trifluoromethylbenzoic acid

Prepared as described in Preparation 1 from methyl 4-ethyl-3-bromobenzoate (1.10 g; 4.52 mmol) and isolated as a white solid (923 mg; 93%).

$^1$H NMR (250MHz; (CD$_3$)$_2$CO) $\delta$: 0.98 (3H, t, J=7 Hz), 2.60 (2H, q, J=7 Hz), 7.36 (1H, d, J=8 Hz), 7.89 and 7.93 (1H, m), 7.96 (1H, br s); $^m/_z$ (API): 217.1 [M–H]$^{74}$.

Preparation 3
4-n-Propyloxy-3-trifluoromethylbenzoic acid

Prepared as described in Preparation I from methyl 3-bromo-4-n-propyloxybenzoate (1.43 g; 5.23 mmol) and isolated as a white solid (1.18 g; 9 1%).

$_1$H NMR (250MHz; (CD$_3$)$_2$SO) $\delta$: 1.09 (3H, t, J=7 Hz), 1.79–1.93 (2H, m), 4.26 (2H, t, J=6 Hz), 7.45 (1H, d, J=9 Hz), 8.19 (1H, d, J=2 Hz), 8.25 and 8.28(1H, dd, J=9, 2 Hz); $^m/_z$ (API$^-$): 203.1 [M–CO$_2$H].

Preparation 4
4-t-Butyl-3-trifluoromethylbenzoic acid

Prepared as described in Preparation I from methyl 3-bromo-4-t-butylbenzoate (2.46 g; 9.1 mmol) and isolated as a white solid (1.55 g; 69%).

$^1$H NMR (250MHz; (CD$_3$)$_2$SO) $\delta$: 1.42 (1H, s), 7.86–7.90 (1H, m), 8.09–8.13 (1H, m), 8.23 (1H, d, J=2 Hz); $^m/_z$ (API$^-$): 245.1 [M–H].

Preparation 5
4-Methoxy-3-trifluoromethylbenzoic acid

Prepared as described in Preparation 1 from methyl 3-bromo-4-methoxybenzoate (6.9 g; 28.1 mmol) and isolated as needles from aq. EtOH (4.61 g; 74%).

$^1$H NMR (250MHz; (CD$_3$)$_2$SO) $\delta$; 3.78 (3H, s), 7.18 (1H, d, J=9 Hz), 7.90 (1H, d, J=2 Hz), 7.98 and 8.02 (1H, dd, J=9, 2 Hz), 12.70–13.10 (1H, br s, exchangeable);

$^m/_z$ (API⁻): 219.1 [M–H]; 175.1 [M–CO$_2$H].

Preparation 6

Methyl 3-Chloro-4-iso-propoxybenzoate

Methyl 3-chloro-4-hydroxybenzoate (5 g, 26.8 mmol) in DMF (45 ml) was treated with potassium carbonate (7.41 g, 53.6 mmol), 2-iodopropane (3.85 ml, 40.2 mmol) and then stirred at 25° C. for 18 h. Work-up with ethyl acetate gave the title compound (6.1 g).

Preparation 7

3-Chloro-4-iso-propoxybenzoic acid

Methyl 3-chloro-4-iso-propoxybenzoate (5.5 g, 24.1 mmol) was hydrolysed using 1M NaOH (36 ml) in methanol (80 ml). Extraction and work-up with ethyl acetate gave the title compound (4.3 g).

$^1$H NMR (DMSO-D$_6$) δ: 1.33 (6H, d), 4.79 (1H, m), 7.24 (1H, d), 7.87 (2H, m).

Preparation 8

3-Bromo-4-ethoxybenzoic acid

The title compound was prepared from 4-ethoxybenzoic acid in a manner similar to that of Procedure 1.

$^1$H NMR (DMSO-D$_6$) δ: 1.45 (3H, t, J=7 Hz), 4.26 (2H, q, J=7 Hz), 7.26 (1H, d, J=9 Hz), 7.98 (1H, dd, J=2, 9 Hz), 8.12 (1H, d, J=2 Hz)

Preparation 9

3-Bromo-4-ethylbenzoic acid

The title compound was prepared from 4-ethylbenzoic acid.

$^1$H NMR (DMSO-D$_6$) δ: 1.20 (3H, t, J=7 Hz), 2.78 (2H, q, J=7 Hz), 7.50 (1H, d, J=8 Hz), 7.90 (1H, dd, J=2, 8 Hz), 8.07 (1H, d, J=8 Hz)

Preparation 10

3-Cyano-4-iso-propylbenzoic acid

The title compound was prepared from 4-iso-propylbenzoic acid similar to that described in Procedure 5.

$^1$H NMR (DMSO-D$_6$) δ: 1.07 (6H, d, J=7 Hz), 3.13 (1H, m, overlapped), 7.48 (1H, d, J=7 Hz), 7.96 (1H, dd, J=2, 8 Hz), 8.00 (1H, d, J=2 Hz).

Preparation 11

4-Methoxy-3-trifluoromethylbenzoic acid

The title compound was prepared from 3-bromo-4-methoxybenzoic acid and potassium trifluoroacetate in a manner similat to that of Procedures 3 and 4.

$^1$H NMR (DMSO-D$_6$) δ: 3.78 (3H, s), 7.18 (1H, d, J=9 Hz), 7.90 (1H, d, J=2 Hz), 8.00 (1H, dd, J=2, 9 Hz), 12.70–13.10 (1H, br, exchangeable)

Preparation 12

4-Methoxy-3-trifluoromethylbenzoyl chloride

The title compound was prepared from 4-methoxy-3-trifluoromethylbenzoic acid with oxalyl chloride and DMF in chloroform at room temperature [D. Levin, Chem. Br., 1977, 20] followed by evaporation in vacuo.

Preparation 13

Methyl 3-Bromo-4-iso-propoxybenzoate

Methyl 3-bromo-4-hydroxybenzoate (2.5 g, 10.8 mmol) in DMF (35 ml) was treated with potassium carbonate (3.0 g, 21.6 mmol), 2-iodopropane (2.76, 21.6 mmol) and then stirred at 25° C. for 48 h. Work-up with ethyl acetate gave the title compound (3.0 g).

$^1$H NMR (250MHz, CDCl$_3$) δ: 1.41 (6H, d, J=7 Hz), 3.89 (3H, s), 4.66 (1H, m), 6.90 (1H, d, J=8 Hz), 7.93 (1H, dd, J=8, 2 Hz), 8.22 (1H, d, J=2 Hz)

Preparation 14

Methyl 3-Cyano-4-iso-propoxybenzoate

Methyl 3-bromo-4-iso-propoxybenzoate (2.0 g, 7.3 mmol) and copper(I)cyanide in N-methyl pyrrolidone (50 ml) were heated under vigorous reflux for 4 h. Work-up with ethyl acetate gave the title compound (1.0 g).

$^1$H NMR (250MHz, CDCl$_3$) δ: 1.56 (6H, d, J=7 Hz), 4.05 (3H, s), 4.88 (1H, m), 7.13 (1H, d, J=8 Hz), 8.31 (1H, dd, J=8, 2 Hz), 8.38 (1H, d, J=2 Hz)

Preparation 15

Methyl 3,5 Dichloro-4-ethoxybenzoate

The title compound was prepared in 69% yield from methyl 3,5-dichloro-4-hydroxybenzoic acid and iodoethane in a manner similar to that of Preparation 6.

$^1$H NMR (250MHz, CDCl$_3$) δ: 1.47 (3H, t, J=7 Hz), 3.91 (3H, s), 4.16 (2H, q, J=7 Hz), 7.96 (2H, s).

Preparation 16

3-Chloro-4-ethoxybenzoic acid $^1$H NMR (DMSO-D$_6$) δ: 1.39 (3H, t, J=7 Hz), 4.20 (2H, q, J=7 Hz), 7.22 (1H, d, J 7 Hz), 7.87 (2H, m).

Preparation 17

3-Bromo-4-iso-propoxybenzoic acid

The title compound was prepared using a method similar to that of Preparation 7.

$^1$H NMR (DMSO-D$_6$) δ: 1.29 (6H, d, J=7 Hz), 4.77 (1H, sep, J=7 Hz), 7.20 (1H, d, J=8 Hz), 7.87 (1H, dd, J=8, 2 Hz), 8.02 (1H, d, J=2 Hz), 12.92 (1H, brs).

Preparation 18

4-iso-Propyloxy-3-trifluoromethylbenzoic acid

Methyl 3-bromo-4-iso-propyloxybenzoate (828 mg; 3.03 mmol) in DMF (25 ml) was treated with potassium trifluoroacetate (922 mg; 6.06 mmol), copper (I) iodide (1.15 g; 6.06 mmol) and toluene (50 ml). The resulting mixture was heated at reflux for 1.5 h (Dean and Stark with removal of ca 50 ml of distillate) followed by reflux for 18 h then cooled. The mixture was poured into Et$_2$O (100 ml) and H$_2$O (100 ml). The two-phase mixture was stirred at room temperature for 0.5 h then filtered through Celite. The two phases were separated, the aq. phase further extracted with EtO (50 ml) and the organic extracts combined, washed with saturated, aq. Na$_2$S$_2$O$_3$, H$_2$O, saturated brine, dried (MgSO$_4$) and evaporated in vacuo to give a brown oil. This was dissolved in MeOH (ca 20 ml) and treated with 2M NaOH (2 ml; 4 mmol) and the resulting solution heated at reflux for 3 h. The volatiles were removed in vacuo and the residue partitioned between EtOAc and H$_2$O. The phases were separated, the aq. phase acidified to pH1 with 2M HCl in the presence of EtOAc and the phases separated. The aq. phase was further extracted with EtOAc, the extracts combined, washed with H$_2$O, saturated brine, dried (MgSO$_4$) and evaporated to dryness in vacuo to give the title compound as a white solid (671 mg; 89%).

$^1$H NMR (250MHz; (CD$_3$)$_2$CO) δ: 1.02 (6H, d, J=6 Hz), 4.53–4.63 (1H, m), 7.01 (1H, d, J=9 Hz), 7.85–7.88 (2H, m); $^m/_z$ (API): 205.0 [M–Pr$^i$].

Preparation 19

4-Ethyl-3-trifluoromethylbenzoic acid

Prepared as described in Preparation 18 from methyl 4-ethyl-3-bromobenzoate (1.10 g; 4.52 mmol) and isolated as a white solid (923 mg; 93%).

$^1$H NMR (250MHz; (CD$_3$)$_2$CO) δ: 0.98 (3H, t, J=7 Hz), 2.60 (2H, q, J=7 Hz), 7.36 (1H, d, J=8 Hz), 7.89 and 7.93 (1H, m), 7.96 (1H, br s); $^m/_z$ (API): 217.1 [M–H].

Preparation 20

4-n-Propyloxy-3-trifluoromethylbenzoic acid

Prepared as described in Preparation 18 from methyl 3-bromo-4-n-propyloxybenzoate (1.43 g; 5.23 mmol) and isolated as a white solid (1.18 g; 91%).

$^1$H NMR (250MHz; (CD$_3$)$_2$SO) δ: 1.09 (3H, t, J=7 Hz), 1.79–1.93 (2H, m), 4.26 (2H, t, J =6 Hz), 7.45 (1H, d, J=9 Hz), 8.19 (1H, d, J=2 Hz), 8.26 (1H, dd, J=9,2 Hz)

Preparation 21
4-t-Butyl-3-trifluoromethylbenzoic acid

Prepared as described in Preparation 18 from methyl 3-bromo-4-t-butylbenzoate (2.46 g; 9.1 mmol) and isolated as a white solid (1.55 g; 69%).

$^1$H NMR (250MHz; (CD$_3$)$_2$SO) δ: 1.42 (9H, s), 7.86–7.90 (1H, m), 8.09–8.13 (1H, m), 8.23 (1H, d, J=2 Hz); $^m/_z$ (API): 245.1 [M–H].

Preparation 22
4-Azidobenzoic acid

To a solution of 4-aminobenzoic acid (2.00 g, 14.00 mmol) in trifluoroacetic acid (10 ml) at 5° C., was added sodium nitrite (3.50 g) portionwise, and the mixture allowed to stir for 30 min. Sodium azide (3.79 g,) was then added portionwise and the mixture stirred for a further 30 min at 0° C. The mixture was diluted with water, and a white solid precipitated. The solid was filtered, washed with cold water and dried, to afford the title compound (1.66 g, 73%).

EXAMPLE 1
N-(6-Methyl-5,6,7,8-tetrahydro[1,6]naphthyridin-3-yl)-3-bromo-4-methoxybenzamide, monohydrochloride 3-Amino-6-methyl-5,6,7,8-tetrahydro[1,6]naphthyridine (300 mg; 1.84 mmol) was dissolved in dry tetrahydrofuran (10 ml) under argon and treated with a solution of 3-bromo-4-methoxybenzoyl chloride (459 mg; 1.84 mmol) in dry tetrahydrofuran (10 ml). The mixture was stirred at ambient temperatures for 18 h and the product (720 mg; 95%) collected by filtration washed with tetrahydrofuran and dried.

$^1$H NMR [250MHz; (CD$_3$)$_2$SO] 67 : 3.03 (3H, s), 3.29 (2H, br m), 3.71 (2H, br m), 4.06 (3H, s), 4.56 (2H, br m), 7.39 (1H, d, J=9 Hz), 8.17–8.21 (2H, m), 8.39 (1H, d, J=2 Hz), 8.91 (1H, d, J=2 Hz); $^m/_z$ (API): 376, 378.

EXAMPLE 2
N-(6-Methyl-5,6,7,8-tetrahydro[1,6]naphthyridin-3-yl)-benzamide

3-Amino-6-methyl-5,6,7,8-tetrahydro[1,6]naphthyridine (314 mg, 1.9 mmol) was dissolved in dichloromethane (10 ml) and treated sequentially with triethylamine (214 mg; 2.1 mmol) and benzoyl chloride (297 mg; 2.1 mmol). The mixture was stirred at ambient temperature until tlc showed no starting material remaining. The reaction mixture was washed with saturated aqueous sodium hydrogen carbonate, water, saturated brine, dried (anhydrous magnesium sulphate) and evaporated to dryness under reduced pressure. Chromatography through silica gel, eluting with methanol in dichloromethane (0 to 50% methanol gradient), gave the title compound as an off-white foam (269 mg; 52%)

$^1$H NMR [250MHz; (CD$_3$)$_2$SO] δ: 2.47 (3H, s), 2.79 and 2.97 (each 2H, t, J=6 Hz), 3.62 (2H, br s), 7.48–7.74 (3H, m), 8.02 (1H, d, J=2 Hz), 8.08–8.11 (2H, m), 8.80 (1H, d, J =2 Hz); $^m/_z$ (API): 268.1 (M+H)$^+$; 266.2 (M–H)$^-$ EXAMPLE 3
N-(6-Methyl-5,6,7,8-tetrahydro[1,6]naphthyridin-3-yl)-2-methoxy-4-t-butylbenzamide, monohydrochloride Prepared as described in Example 1, using 4-t-butyl-2-methoxybenzoyl chloride, in 89% yield.

$^1$H NMR [250MHz, (CD$_3$)$_2$SO] δ: 1.21 (9H, s), 2.80 (3H, s), 3.05 (2H, br m), 3.46 (2H, br m), 3.83 (3H, s), 4.32 (2H, br m), 6.97–7.02 (2H m), 7.49 (1H, d, J=8 Hz), 7.99 (1H, br d), 8.61 (1H, d, J=2 Hz), 10.19 (1H, s, exchangeable), 10.90–11.40 (1H, br, exchangeable); $^m/_z$ (API): 352.3 (M–H)$^-$ EXAMPLE 4
N-(6-Methyl-5,6,7,8-tetrahydro[1,6]naphthyridin-3-yl)-4-iso-propoxybenzamide, monohydrochloride Prepared as described in Example 1 from 4-isopropyloxybenzoyl chloride in 91% yield.

$^1$H NMR [250MHz, (CD$_3$)$_2$SO)] δ: 1.14 (6H, d, J=6 Hz), 2.75 (3H, s), 2.93 (2H, br m), 3.53 (2H, br m), 4.23 and 4.34 (each 1H, 2 br m's), 4.54–4.63 (1H, m), 6.89 (2H, d, J=9 Hz), 7.88 (2H, d, J=9 Hz), 7.94 (1H, d, J=2 Hz), 8.63 (1H, d, J=2 Hz), 10.25 (1H, s, exchangeable), 11.00 (1H, br s, exchangeable); $^m/_z$ (API): 324.2 (M–H)$^-$ EXAMPLE 5
N-(6-Methyl-5,6,7,8-tetra hydro[1,6]naphthyridin-3-yl)-4-ethoxybenzamide, monohydrochloride Prepared as described in Example 1 from 4-ethoxybenzoyl chloride in 92% yield.

$^1$H NMR [250MHz, (CD$_3$)$_2$SO] δ: 1.54 (3H, t, J=7 Hz), 3.10 (3H, s), 3.34 (2H, br m), 3.78 (2H, br m), 4.31 (2H, q, J=7 Hz), 4.62 (2H, br m), 7.25 (2H, d, J=9 Hz), 8.18 (2H, d, J=9 Hz), 8.29 (1H, d, J=2 Hz), 8.98 (1H, d, J=2 Hz), 10.61 (1H, s, exchangeable), 11.35 (1H, br s, exchangeable); $^m/_z$ (API): 310.2 (M–H)$^-$ EXAMPLE 6
N-(6-Methyl-5,6,7,8-tetrahydro[1,6]naphthyridin-3-yl)-2-methoxy-5-pivaloylbenzamide, monohydrochloride Prepared as described in Example 1 from 2-methoxy-5-pivaloylbenzoyl chloride in 91% yield.

$^1$H NMR [250MHz, (CD$_3$)$_2$SO] δ: 1.34 (9H, s), 2.93 (3H, s), 3.12 (2H, br m), 3.71 (2H, br m), 3.98 (3H, s), 4.41 and 4.52 (each 1H, 2 br m's), 7.28 (1H, d, J=9 Hz), 8.06–8.12 (3H, m), 8.75 (1H, br d), 10.49 (1H, s, exchangeable), 11.30–11.70 (1H, br, exchangeable); $^m/_z$ (API): 382 (M+H)$^+$ EXAMPLE 7
N-(6-Methyl-5,6,7,8-tetrabydro[1,6]naphthyridin-3-yl)-3-trifuoro methyl benzamide, monohydrochloride Prepared as described in Example 1 from 3-trifluoromethylbenzoyl chloride in 91% yield.

$^1$H NMR [250MHz, (CD$_3$)SO] δ: 2.89 (3H, s), 3.15 (2H, br m), 3.55 (2H, br m), 4.42 (2H:, br m), 7.70–8.31 (5H, m), 8.78 (1H, d, J=2 Hz); $^m/_z$ (API): 336.2 (M+H)$^+$

EXAMPLE 8
N-(6-Benzyl-5,6,7,8-tetrahydro[1,6]naphthyridin-3-yl)-3-bromo-4methoxybenzamide 3-Bromo-4-methoxybenzoic acid (270 mg; 1.17 mmol) was dissolved in N,N-dimethylformamide (5 ml), the solution was cooled to 0–5° C. and treated with 1-hydroxybenzotriazole(158 mg; 1.17 mmol) then 1-(3-dimethylaminopropyl)-3-ethylcarbodiimide hydrochloride (224 mg; 1.17 mmol) and the mixture stirred at 0–5° C. for 0.5 h and treated with a solution of 3-amino-6-benzyl-5,6,7,8-tetrahydro[1,6]naphthyridine (255 mg; 1.06 mmol) in DMF (5 ml). The reaction mixture was stirred at ambient temperature for 72 h then diluted with dichloromethane (100 ml). The resulting mixture was washed with water (5×25 ml), saturated brine, dried (anhydrous magnesium sulfate) and evaporated to dryness in vacuo to yield a mobile, brown oil, which on trituration under 60–80° C. petroleum ether gave a biege powder, which was collected by filtration, washed with 60–80° C. petroleum ether and dried in air. Recrystallisation from ethyl acetate 60–80° C. petroleum ether gave the title compound as a beige powder (236 mg; 49%), m.p. 214–215° C.

$^1$H NMR [250MHz, (CD$_3$)$_2$SO] δ: 2.80, 2.87, 3,62 and 3.72 (each 2H, 4 br m), 3.95 (3H, s), 7.27 (1H, d, J=9 Hz), 7.34–7.39 (5H, m), 7.87 (1H, br s), 8.00 and 8.04 (1H, dd, J=9 and 2 Hz), 8.24 (1H, d, J=2 Hz), 8.65 (1H, d, J=2 Hz).

$^m/_z$ Found 451.0895. C$_{23}$H$_{22}$BrN$_3$O$_2$ requires 451.0895. Found: Br, 17.90% C$_{23}$H$_{22}$BrN$_3$O$_2$ requires: Br, 17.66%.

The following Examples were prepared in a manner similar to that of Example 1.

EXAMPLE 9
N-(6-Methyl-5,6,7,8-tetrahydro[1,6]naphthyridin-3-yl)-4-methoxy-3-trifluoromethylbenzamide, monohydrochloride $^1$H NMR [250MHz; D$_2$O] δ: 3.11 (3H, s), 3.26 (2H, br m), 3.40–4.10 (2H, br m), 3.87 (3H, s), 4.30–4.70 (2H, br m), 7.17 (1H, d, J=9 Hz), 7.92 (1H, m), 7.98–7.80 (2H, m), 8.50 (1H, d, J=2 Hz); $^m/_z$ (API): 366.1 [M+H]

EXAMPLE 10
N-(6-Methyl-5,6,7,8-tetrahydrol[1,6]naphthyridin-3-yl)-4-t-butylbenzamide, monihydrochloride $^1$H NMR [250MHz; (CD$_3$)$_2$SO] δ: 1.27 (9H, s), 3.10 (3H, s), 3.22 (2H, br m), 3.75 (2H, br m), 4.50 (2H, br m), 7.56 (2H, d, J=8 Hz), 7.75 (2H, d, J=8 Hz), 7.93 (1H, d, J=2 Hz), 8.56 (1H, d, J=2 Hz); $^m/_z$ (API): 324.2 [M+H]$^+$

EXAMPLE 11
N-(6-Methyl-5,6,7,8-tetrahydro[1,6]naphthyridin-3-yl)-3-bromo-4-ethoxybenzamide, monohydrochloride $^1$H NMR [250MHz; (CD$_3$)$_2$SO] δ: 1.34 (3H, t, J=7 Hz), 3.16 (3H, br s), 3.23 (2H, br m), 3.40–4.15 (2H, br m), 4.02 (2H, q, J=7 Hz), 4.54 (2H, br), 6.92 (1H, d, J=9 Hz), 7.62 and 7.65 (1H, dd, J=9 and 2 Hz), 7.78 (1H, d, J=2 Hz), 7.86 (1H, d, J=2 Hz), 8.41 (1H, d, J=2 Hz); $^m/_z$ (API): 390 (M); 392 [M+H]$^+$

EXAMPLE 12
N-(6-Methyl-5,6,7,8-tetrahydro[1,6]naphthyridin-3-yl)-3-bromo-4-iso-propyloxybenzamide, monohydrochloride $^1$H NMR [250MHz; (CD$_3$)$_2$SO] δ: 1.28 (6H, d, J=6 Hz), 3.07 (3H, s), 3.19 (2H, br), 3.35–4.00 (2H, br), 4.47 (2H, br), 4.55–4.75 (1H, m), 7.05 (1H, d, J=9 Hz), 7.66 and 7.70 (1H, dd, J=9 and 2 Hz), 7.84 (1H, d, J=2 Hz), 7.86 (1H, d, J=2 Hz), 8.44 (1H, d, J=2 Hz); $^m/_z$ (API): 404.1 (M)$^+$, 406 (M+H)$^+$

EXAMPLE 13
N-(6-Methyl-5,6,7,8-tetrahydro[1,6]naphthyridin-3-yl)-3-chloro-4-methoxybenzamide, hydrochloride $^1$H NMR [250MHz; D$_2$O] δ: 2.97 (3H, s), 3.05 (2H, br), 3.20–4.00 (2H, br), 4.36 (2H, br), 4.68 (3H, s), 6.79 (1H, d, J=9 Hz), 7.44–7.47 (2H, m), 7.65 (1H, br s), 8.17 (1H, br s); $^m/_z$ (API): 332.2 [M+H]$^+$

EXAMPLE 14
N-(6-Methyl-5,6,7,8-tetrahydro[1,6]naphthyridin-3-yl)-4-ethyl benzamide Prepared as described in Example 1 from 4-ethylbenzoyl chloride, purified by chromatography of the free base through SiO$_2$, eluting with mixtures of methanol in dichloromethane, and isolated in 23% yield.

$^1$H NMR [250MHz; CD$_3$OD] δ: 1.09 (3H, t, J=8 Hz), 2.32 (3H, s), 2.56 (2H, q, J=8 Hz), 2.69 (2H, t, J=6 Hz), 2.84 (2H, t, J=6 Hz), 3.49 (2H, s), 7.19 (2H, d, J=8 Hz), 7.70 (2H, d, J=8 Hz), 7.81 (1H, d, J=2 Hz), 8.48 (1H, d, J=2 Hz);

$^m/_z$ (API): 296.2 [M+H]$^+$

EXAMPLE 15
N-(6-Methyl-5,6,7,8-tetrahydro[1,6]naphthyridin-3-yl)-4-cyclohexylbenzamide Prepared as described in Example 1 from 4-cyclohexylbenzoyl chloride and purified as described in Example 15. The title compound was isolated in 70% yield as the free base.

$^1$H NMR [250MHz; CD$_3$OD] δ: 1.20–1.26 (5H, m), 1.70–2.00 (5H, m), 2.48 (3H, s), 2.50–2.70 (1H, m), 2.84 (2H, t, J=6 Hz), 3.00 (2H, t, J=6 Hz), 3.65 (2H, s), 7.34 (2H, d, J=8 Hz), 7.86 (2H, d, J=8 Hz), 7.96 (1H, d, J=2 Hz), 8.67 (1H, d, J=2 Hz);

$^m/_z$ (API): 350.2 [M+H]$^+$

EXAMPLE 16
N-(6-Methyl-5,6,7,8-tetrahydro[1,6]naphthyridin-3-yl)-4-benzoylbenzamide Prepared as described in Example 1. The crude hydrochloride salt was dissolved in water, neutralised with saturated aqueous sodium hydrogen carbonate and the free base extracted into dichloromethane. The organic extracts were combined, washed with saturated brine, dried (magnesium sulphate) and evaporated to dryness to give the title compound in 71% yield.

1H NMR [250MHz; CD$_3$OD] δ: 2.45 (3H, s), 2.81 (2H, t, J=6 Hz), 2.97 (2H, t, J=6 Hz), 3.62 (2H, s), 7.08–8.04 (1OH, m), 8.63 (1H, d, J=2 Hz); $^m/_z$ (API): 372.2 [M+H]$^+$

EXAMPLE 17
N-(6-Methyl-5,6,7,8-tetrahydro[1,6]naphthyridin-3-yl)-2,3-dihydrobenzofuran-5-ylcarboxamide Prepared as described in Example 1 from 2,3-dihydrobenzofuran-5-yl-carbonyl chloride and purified as described in Example 15 to give the title compound in 16% yield.

1H NMR [250MHz; CD$_3$OD] δ: 2.39 (3H, s), 2.75 (2H, t, J=6 Hz), 2.90 (2H, t, J=6 Hz), 3.15 (2H, t, J=9 Hz), 3.54 (2H, s), 4.53 (2H, t, J=9 Hz), 6.70 (1H, d, J=8 Hz), 7.63 and 7.67 (1H, dd, J=8 and 2 Hz), 7.71 (1H, br), 7.84 (1H, d, J=2 Hz), 8.52 (1H, d, J 2 Hz); $^m/_z$ (API): 310.2 [M+H]$^{30}$

EXAMPLE 18
N-(6-Methyl-5,6,7,8-tetrahydro[1,6]naphthyridin-3-yl)-4-t-butyl-3-trifluoromethylbenzamide Prepared as described in Example 1 from 4-t-butyl-3-trifluoromethyl chloride and purified as described in Example 15. The title compound was obtained in 63% yield.

$^1$H NMR [250MHz; (CD$_3$)$_2$SO] δ: 1.37 (9H, s), 2.28 (3H, s), 2.61 (2H, t, J=6 Hz), 2.78 (2H, m), 3.44 (2H, s), 7.80–7.85 (2H, m), 8.08–8.18 (1H, m), 8.24 (1H, m), 8.59 (1H, d, J=2 Hz); $^m/_z$ (API): 390.2 [M–H]$^+$

EXAMPLE 19
N-(6-Methyl-5,6,7,8-tetrahydro[1,6]naphthyridin-3-yl)-4-iso-propylbenzamide, hydrochloride $^1$H NMR [250MHz; (CD$_3$)$_2$SO] δ: 1.19 (6H, d, J=7 Hz), 2.87–2.96 (1H, m), 3.06 (3H, s), 3.21 (2H, br m), 3.40–3.90 (2H, m), 4.48 (2H, br m), 7.40 (2H, d, J=8 Hz), 7.74 (2H, d, J=8 Hz), 7.92 (1H, d, J=2 Hz), 8.54 (1H, d, J=2 Hz); $^m/_z$ (API): 310.2 [M+H]$^+$

EXAMPLE 20
N-(6-Methyl-5,6,7,8-tetrahydro[1,6]naphthyridin-3-yl)-4-ethoxy-3-nitrobenzamide hydrochloride $^1$H NMR [250MHz; (CD$_3$)$_2$SO] δ: 1.15 (3H, t, J=7 Hz), 2.94 (3H, s), 3.05 (2H, br m), 3.56 (2H, br m), 3.97 (2H, q, J=7 Hz), 4.34 (2H, br m), 7.02 (1H, d, J=9 Hz), 7.71 (1H, m), 7.74 and 7.78 (1H, dd, J=9 and 2 Hz), 8.02 (1H, d, J=2 Hz), 8.25 (1H, d, J=2 Hz);

$^m/_z$ (API): 357.1 [M+H]$^+$

EXAMPLE 21
N-(6-Methyl-5,6,7,8-tetrahydro[1,6]naphthyridin-3-yl)-3-bromo-4-1-butylbenzamide, hydrochloride $^1$H NMR [250MHz; (CD$_3$)$_2$SO] δ: 1.16 (9H, s), 2.93 (3H, s), 2.93–3.20 (2H, br m), 3.54 (2H, br m), 4.32 (2H, br m), 7.23 (1H, d, J=8 Hz), 7.55–7.58 (1H, br m), 7.76 (1H, br), 7.81 (1H, br), 8.38 (1H, br); $^m/_z$ (API) 402.1, 404.0 (M)$^+$

EXAMPLE 22
N-(6-Methyl-5,6,7,8-tetrahydro[1,6]naphthyridin-3-yl)-3-bromo-4-ethylbenzamide, hydrochloride $^1$H NMR [250MHz; $(CD_3)_2SO$] δ: 0.94 (3H, t, J=7 Hz), 2.30–2.60 (2H, m), 2.90–3.28 (5H, m), 3.59 (2H, br m), 4.40 (2H, br m), 7.05 (1H, d, J=8 Hz), 7.50–7.65 (1H, m), 7.73 (1H, d, J=1 Hz), 7.81 (1H, m), 8.36 (1H, d, J=2 Hz); $m/_z$ (API) 374.0, 376.0 (M$^+$)

EXAMPLE 23
N-(6-Methyl-5,6,7,8-tetrahydro[1,6]naphthyridin-3-yl)-3-cyano-4-methoxybenzamide, hydrochloride $^1$H NMR [250MHz; $(CD_3)_2SO$] δ: 3.22 (3H, s), 3.25–3.45 (2H, m), 3.60–3.95 (2H, m), 3.97 (3H, s), 4.64 (2H, br m), 7.20 (1H, d, J=9 Hz), 7.90–8.20 (3H, m), 8.46 (1H, m); $m/_z$ (API): 323.1 (M+H)$^+$

EXAMPLE 24
N-(6-Methyl-5,6,7,8-tetrahydro[1,6]naphthyridin-3-yl)-3-bromo-4-n-propyl-oxybenzamide, hydrochloride $^1$H NMR [250MHz; $(CD_3)_2SO$] δ: 1.01 (3H, t, J=7 Hz), 1.73–1.76 (2H, m), 3.10–3.40 (5H, m), 3.55–4.10 (4H, 2m), 4.40–4.80 (2H, m), 6.89 (1H, d, J=9 Hz), 7.68 and 7.71 (2×1H, m), 7.88 (1H, d, J=2 Hz), 7.94 (1H, m), 8.51 (1H, d, J=2 Hz); $m/_z$ (API): 404.1, 406.0 (M$^+$)

EXAMPLE 25
N-(6-Methyl-5,6,7,8-tetrahydro[1,6]naphthyridin-3-yl)-3,5-dichloro-4-methoxybenzamide, hydrochloride $^1$H NMR [250MHz; $(CD_3)_2SO$] δ: 3.13 (3H, s), 3.20–3.40 (2H, m), 3.50–4.10 (2H, br m), 3.82 (3H, s), 4.40–4.70 (2H, br m), 7.68 (2H, s), 7.89 (1H, d, J=2 Hz), 8.49 (1H, d, J=2 Hz); $m/_z$ (API): 366.1 (MH$^⊕$)

EXAMPLE 26
N-(6-Methyl-5,6,7,8-tetrahydro[1,6]naphthyridin-3-yl)-3-bromo-4-iso-propylbenzamide, hydrochloride $^1$H NMR [250MHz; $(CD_3)_2SO$] δ: 1.17 (6H, d, J=7 Hz), 3.18 (3H, s), 3.20–3.40 (3H, m), 3.50–4.10 (2H, br m), 4.40–4.70 (2H, br m), 7.40 (1H, d, J=8 Hz), 7.80 and 7.84 (2×1H, m), 8.02 (1H, d, J=1 Hz), 8.09 (1H, m), 8.71 (1H, d, J=2 Hz); $m/_z$ (API): 386.1, 388.1 (MH$^⊕$).

EXAMPLE 27
N-(6-Methyl-5,6,7,8-tetrahydro[1,6]naphthyridin-3-yl)-4-n-propyloxy-3-trifluoromethylbenzamide, hydrochloride $^1$H NMR [250MHz; $(CD_3)_2SO$] δ: 0.75 (3H, t, J=7 Hz), 1.40–1.60 (2H, m), 2.95 (3H, s), 2.30–3.10 (2H, br m), 3.30–3.90 (4H, br m), 4.20–4.60 (2H, br m), 6.80 (1H, d, J=9 Hz), 7.70–7.90 (4H, m), 8.34 (1H, br s); $m/_z$ (API): 394.1 (M+H$^+$)

EXAMPLE 28
N-(6-Methyl-5,6,7,8-tetrahydro[1,6]naphthyridin-3-yl)-3-iodo-4-methoxybenzamide hydrochloride $^1$H NMR [250MHz; $(CD_3)_2SO$] δ: 3.20 (3H, s), 3.34 (2H, br m), 3.85 (3H, s), 3.60–4.10 (2H, br m), 4.50–4.80 (2H, br m), 6.95 (1H, d, J=9 Hz), 7.79 and 7.82 (1H, dd, J=9, 2 Hz), 7.96 (1H, d, J=2 Hz), 8.12 (1H, d, J=2 Hz), 8.51 (1H, d, J=2 Hz); $m/_z$ (API): 424.0 (M+H$^+$).

EXAMPLE 29
N-(6-Methyl-5,6,7,8-tetrahydro[1,6]naphthyridin-3-yl)-4-iso-propyl-3-trifluoromethylbenzamide, hydrochloride $^1$H NMR [250MHz; $(CD_3)_2SO$] δ: 0.87 (6H, d, J=7 Hz), 2.80–3.10 (6H, m), 3.20–3.80 (2H, br m), 4.10–4.50 (2H, m), 7.33 (1H, d, J=8 Hz), 7.60–7.80 (3H, m), 8.32 (1H, d); $m/_z$ (API): 378.1 (MH$^⊕$), 376.2 [M–H].

EXAMPLE 30
N-(6-Methyl-5,6,7,8-tetrahydro[1,61naphthyridin-3yl)-3-cyano-4-n-propyloxybenzamide, hydrochloride $^1$H NMR [250MHz; $(CD_3)_2SO$] δ: 0.97 (3H, t, J=7 Hz), 1.65–1.81 (2H, m), 3.15 (3H, s), 3.20–3.50 (2H, m), 3.50–4.20 (2H, m), 4.05 (2H, t, J=7 Hz), 4.40–4.80 (2H, m), 7.11 (1H, d, J=9 Hz), 7.91–7.99 (2H, m), 8.08 (1H, d, J=2 Hz), 8.64 (1H, d, J=2 Hz);

$m/_z$ (API): 351.2 (MR$^⊕$), 307.2 [M–Pr]

EXAMPLE 31
N-(6-Methyl-5,6,7,8-tetrahydro[1,6]naphthyridin-3-yl)-3-cyano-4-ethoxybenzamide, hydrochloride $^1$H NMR [250MHz; $(CD_3)_2SO$] δ: 1.25 (3H, t, J=7 Hz), 2.99 (3H, s), 3.10–4.00 (41H, m), 4.09 (2H, q, J=7 Hz), 4.20–4.90 (2H, m), 7.06 (1H, d, J=10 Hz), 7.90–7.94 (21H, m), 8.08 (1H, d, J=2 Hz), 8.71 (1H, d, J=2 Hz); $m/_z$ (API$^+$): 337.2 (MH), 307.2 [M–Et].

EXAMPLE 32
N-(6-Methyl-5,6,7,8-tetrahydro[1,6]naphthyridin-3-yl)-3-chloro-4-ethoxybenzamide, hydrochloride $^1$H NMR [250MHz; $(CD_3)_2SO$] δ: 1.08 (3H, t, J=7 Hz), 2.90 (3H, s), 2.90–3.15 (2H, br m), 3.25–3.70 (21H, br m), 3.77 (2H, q, J=7 Hz), 4.10–4.50 (2H, br m), 6.69 (1H, d ,J=9 Hz), 7.31–7.35 (21H, m), 7.63 (1H, d, J=2 Hz), 8.19 (1H, d, J=2 Hz);

$m/_z$ (API$^+$): 346.1 (MH), 344.3 [M–H]

EXAMPLE 33
N-(6-Methyl-5,6,7,8-tetrahydro[1,6]naphthyridin-3-yl)-3-chloro-4-iso-propyloxybenzamide, hydrochloride $^1$H NMR [250MHz; $(CD_3)_2SO$] δ: 1.35 (6H, d, J=6 Hz), 3.14 (3H, s), 3.32 (2H, br m), 3.45–3.90 (2H, br m), 4.40–4.70 (2H, br m), 4.69 (1H, m), 7.16 (1H, d, J=9 Hz), 7.70–7.74 (1H, dd, J=9, 2 Hz), 7.79 (1H, d, J 2 Hz), 8.01 (1H, d, J=2 Hz), 8.63 (1H, d, J=2 Hz); $m/_z$ (API$^+$): 360.1 (MH).

EXAMPLE 34
N-(6-Methyl-5,6,7,8-tetrahydro[1,6]naphthyridin-3-yl)-3-fluoro-4-methoxybenzamide, hydrochloride $^1$H NMR [250MHz; $(CD_3)_2SO$] δ: 3.09 (3H, s), 3.15–3.30 (2H, br m), 3.40–4.00 (2H, br m), 3.82 (3H, s), 4.35–4.70 (2H, br m), 7.06 (1H, t, J=9 Hz), 7.43 and 7.47 (1H, dd, J 12,2 Hz), 7.56 (1H, br d, J=9 Hz),7.90 (1H, d, J=2 Hz), 8.46 (1H, d, J=2 Hz);

$m/_z$ (API$^+$): 314.2 [M–H], 316.1 (MH).

EXAMPLE 35
N-(6-Methyl-5,6,7,8-tetrahydro[1,6]naphthyridin-3-yl]-4-ethyl-3-trifluoromethylbenzamide Prepared as described in Example 1 from 4-ethyl-3-trifluoromethyl benzoyl chloride in 48% yield. Basification and purification by chromatography through SiO$_2$, eluting with a mixture of containing 10% 0.880 aq. NH, in MeOH and DCM (1:9), gave the title compound as the free base in 16% yield.

$^1$H NMR [250MHz; $CD_3OD$] δ: 1.19 (3H, t, J=7 Hz), 2.40 (3H, s), 2.68–2.84 (4H, m), 2.92 (2H, t, J=6 Hz), 3.58 (2H, br s), 7.51 (1H, d, J=8 Hz), 7.90 (1H, d, J=2 Hz), 8.01 and 8.04 (1H, br dd), 8.14 (1H, br d), 8.56 (1H, d, J=2 Hz);

$m/_z$ (API$^+$): 362.2 [M–H], 364.2 (MH).

EXAMPLE 36
N-(6-Methyl-5,6,7,8-tetrahydro[1,6]naphthyridin-3-yl)-4-iso-propyloxy-3-trifluoromethylbenzamide, hydrochloride ¹H NMR [250MHz; (CD₃)₂SO] δ: 1.14 (6H, d, J=6 Hz), 2.95–3.25 (5H, m), 3.40–4.00 (2H, br m), 4.20–4.60 (3H, br m), 6.96 (1H, d, J=9 Hz), 7.75–7.95 (3H, m), 8.44 (1H, br s); $m/z$ (API⁺): 394.1 (MH), 350.1 [M–Pr]⁻].

EXAMPLE 37
N-(6-Methyl-5,6,7,8-tetrahydro[1,6]naphthyridin-3-yl)-3-iodo-4-methylbenzamide hydrochloride ¹H NMR [250MHz; (CD₃)₂SO] δ: 2.60 (3H, s), 3.09 (3H, brd), 3.10–3.80 (4H, m), 4.55, 4.71 (2H, br m), 7.67 (1H, d, J=9 Hz), 8.10 (1H, dd, J=9,2 Hz), 8.35 (1H, d, J=2 Hz), 8.59 (1H, d, J=2 Hz), 9.00 (1H, d, J=2 Hz), 10.84 (1H, s), 11.13 (1H, br);

$m/z$ (API⁺): 408.0 (MH⁺, 88%)

EXAMPLE 38
N-(6-Methyl-5,6,7,8-tetrahydro[1,6]naphthyridin-3-yl)-4-azido-3-iodo-benzamide Prepared from D4 in a manner similar to that described in Example 8 and P22.

$m/z$ (API⁺): 435.2 (MH+, 85%).

EXAMPLE 39
N-(2-Bromo-6-methyl-5,6,7,8-tetrahydro[1,6]naphthyridin-3-yl)-3-bromo-4-ethoxybenzamide The title compound was prepared in 6% yield from D6.

¹H NMR (250MHz, d₆DMSO) δ: interalia 1.34 (3H, t, J=7 Hz), 2.36 (3H, s), 2.73 (2H, m), 2.85 (2H, m), 3.52 (2H, s), 4.16 (2H, q, J=7 Hz), 7.20 (1H, d, J=8 Hz), 7.95 (1H, dd, J=8, 2 Hz), 8.18 (1H, d, J=2 Hz), 10.09 (1H, s); m/z (API⁺): 468/470/472 (MH⁺).

EXAMPLE 40
N-(2-Bromo-6-methyl-5,6,7,8-tetrahydro[1,6]naphthyridin-3-yl)-4-methoxy-3-trifluoromethylbenzamide, hydrochloride The title compound was prepared in 16% yield from the amine D6.

¹H NMR [free base] (250MHz, CDCl₃) 3: 2.49 (3H, s), 2.78 (2H, t, J=6 Hz), 3.03 (2H, t, J=6 Hz), 3.60 (2H, s), 4.01 (3H, s), 7.14 (1H, d, J=9 Hz), 8.08 (1H, dd, J=9,2 Hz), 8.16 (1H, d, J=2 Hz), 8.32 (1H, brs), 8.49 (1H, s); m/z (API⁺): 444/446 (MH⁺).

EXAMPLE 41
N-(2,6-Dimethyl-5,6,7,8-tetrahydro[1,6]naphthyridin-3-yl)-3-bromo-4-ethoxy-benzamide The title compound was prepared in 36% yield from the amine D7.

¹H NMR (250MHz, CDCl₃) δ: 1.52 (3H, t, J 7 Hz), 2.49 (3H, s), 2.53 (3H, s), 2.78 (2H, t, J=6 Hz), 3.00 (2H, t, J=6 Hz), 3.55 (2H, s), 4.19 (2H, q, J=7 Hz), 6.96 (1H, d, J=8 Hz), 7.76–7.84 (3H, m), 8.06 (1H, d, J=2 Hz); m/z (API⁺): 404/406 (MH⁺).

EXAMPLE 42
N-(2,6-Dimethyl-5,6,7,8-tetrahydro[1,6]naphthyridin-3-yl)-4-methoxy-3-trinfluoromethylbenzamide.

The title compound was prepared in 29% from the amine D7.

¹H NMR (250MHz, CDCl₃) δ: 2.48 (3H, s), 2.53 (3H, s), 2.78 (2H, t, J=6 Hz), 3.01 (2H, t, J=6 Hz), 3.56 (2H, s), 4.00 (3H, s), 7.12 (1H, d, J=8 Hz), 7.73 (1H, brs), 7.82 (1H, s), 8.04–8.09 (2H, m); m/z (API⁺): 380 (MH⁺).

EXAMPLE 43
N-(2-Cyano-6-methyl-5,6,7,8-tetrahydro[1,6]naphthyridin-3-yl)-4-methoxy-3-trifluoromethylbenzamide A sample of the compound prepared in Example 40 (86 mg, 0.19 mmol) was dissolved in N-methylpyrrolidinone (2 ml) and copper (I) cyanide (50 mg) added. The mixture was heated in an oil bath at 180° C. under argon for 5 h. After cooling, the mixture was diluted with water and ethyl acetate, filtered and the organic layer washed with brine, dried (MgSO₄) and evaporated to an oil. Purification by chromatography on silica gel eluting with dichloromethane:methanol: aq ammonia (0.880) gave the title compound as a white solid (7.5 mg).

¹H NMR (250MHz, CDCl₃) δ: 2.51 (3H, s), 2.80 (2H, t, J=6 Hz), 3.05 (2H, t, J=6 Hz), 3.69 (2H, s), 4.01 (3H, s), 7.14 (1H, d, J=9 Hz), 8.06 (1H, dd, J=9, 2 Hz), 8.20 (1H, d, J =2 Hz), 8.28 (1H, brs), 8.55 (1H, s); m/z (API⁺): 391 (MH⁺).

EXAMPLE 44
N-(2-Chloro-6-methyl-5,6,7,8-tetrahydro[1,6]naphthyridin-3-yl)-3-bromo-4-ethoxybenzamide ¹H NMR (CDCl₃) δ: 1.53 (3H, t), 2.50 (2H, s), 2.78 (2H, t), 3.01 (2H, t), 3.62 (2H, s), 4.20 (2H, q), 6.98 (1H, d), 7.81 (1H, dd), 8.11 (1H, d), 8.25 (1H, s), 8.52 (1H, s); m/z (API⁺): 424.1 (M⁺; 100%).

EXAMPLE 45
N-(2-Chloro-6-methyl-5,6,7,8-tetrahydro[1,6]naphthyridin-3-yl)-4-methoxy-3-trifluoromethylbenzamide ¹H NMR (CDCl₃) δ: 2.51 (3H, s), 2.79 (2H, t), 3.02 (2H, t), 3.63 (2H, s), 4.01 (3H, s), 7.14 (1H, d), 8.06 (1H, dd), 8.15 (1H, d), 8.26 (1H, s), 8.55 (1H, s);

m/z (API⁺): 400.2 (MH⁺, 100%).

Biological Data

All the compounds showed in vitro binding affinity in this test with pKi's in the range 6–9. Examples 1, 3, 10, 11, 12, 20, 28, 30, 33 and 36 had a pKi>8.0.

Binding Assay Method

WO 92/22293 (SmithKline Beecham) discloses compounds having anti-convulsant activity, including inter alia the compound trans-(+)-6-acetyl-4S-(4-fluorobenzoylamino)-3,4-dihydro-2,2-dimethyl-2H-1-benzopyran-3R-ol (herein referred to as Compound A). It has been found that the compounds of WO 92/22293 bind to a novel receptor obtainable from rat forebrain tissue, as described in WO 96/18650 (SmithKline Beecham). The affinity of test compounds to the novel receptor site is assessed as follows.

Method

Whole forebrain tissue is obtained from rats. The tissue is first homogenised in buffer (usually 50 mM Tris/HCl, pH 7.4). The homogenised tissue is washed by centrifugation and resuspension in the same buffer, then stored at −70° C. until used.

To carry out the radioligand binding assay, aliquots of tissue prepared as above (usually at a concentration of 1–2 mg protein/ml) are mixed with aliquots of [3H]-Compound A dissolved in buffer. The final concentration of [3H]-Compound A in the mixture is usually 20 nM. The mixture is incubated at room temperature for 1 hour. [3H]-Compound A bound to the tissue is then separated from unbound [3H]-Compound A by filtration through Whatman GF/B glass fibre filters. The filters are then washed rapidly with ice-cold buffer. The amount of radioactivity bound to the tissue trapped on the filters is measured by addition of liquid scintillation cocktail to the filters followed by counting in a liquid scintillation counter.

In order to determine the amount of "specific" binding of [3H]-Compound A, parallel assays are carried out as above in which [3H]-Compound A and tissue are incubated together in the presence of unlabelled Compound A (usually 3 μM). The amount of binding of [3H]-Compound A remaining in the presence of this unlabelled compound is defined as "non-specific" binding. This amount is subtracted from the total amount of [3H]-Compound A binding (i.e. that present in the absence of unlabelled compound) to obtain the amount of "specific" binding of [3H]-Compound A to the novel site.

The affinity of the binding of test compounds to the novel site can be estimated by incubating together [3H]-Compound A and tissue in the presence of a range of concentrations of the compound to be tested. The decrease in the level of specific [3H]Compound A binding as a result of competition by increasing concentrations of the compound under test is plotted graphically, and non-linear regression analysis of the resultant curve is used to provide an estimate of compound affinity in terms of pKi value.

MEST Test

The maximal electroshock seizure (MEST) threshold test in rodents is particularly sensitive for detecting potential anticonvulsant properties[1]. In this model, anticonvulsant agents elevate the threshold to electrically-induced seizures whilst proconvulsants lower the seizure threshold.

Method

Mice (naive male, Charles River, U.K. CD-1 strain, 25–30 g) are randomly assigned to groups of 10–20 and dosed orally or intraperitoneally at a dose volume of 10 ml/kg with various doses of compound (0.3–300 mg/kg) or vehicle. Mice are then subjected at 30 or 60 min post dose to a single electroshock (0.1 sec, 50 Hz, sine wave form) administered via corneal electrodes. The mean current and standard error required to induce a tonic seizure in 50% ($CC_{50}$) of the mice in a particular treatment group is determined by the 'up and down' method of Dixon and Mood (1948)[2]. Statistical comparisons between vehicle- and drug-treated groups are made using the method of Litchfield and Wilcoxon (1949)[3].

In control animals the $CC_{50}$ is usually 14–18 mA. Hence the first animal in the control group is subjected to a current of 16 mA. If a tonic seizure does not ensue, the current is increased for a subsequent mouse. If a tonic convulsion does occur, then the current is decreased, and so on until all the animals in the group have been tested.

The percentage increase or decrease in $CC_{50}$ for each group compared to the control is calculated.

Studies are carried out using a Hugo Sachs Electronik Constant Current Shock Generator with totally variable control of shock level from 0 to 300 mA and steps of 2 mA are usually used.

Drugs are suspended in 1% methyl cellulose.

REFERENCES

1. Loscher, W. and Schmidt, D. (1988). Epilepsy Res., 2, 145–181
2. Dixon, W. J. and Mood, A. M. (1948). J. Amer. Stat. Assn., 43, 109–126
3. Litchfield, J. T. and Wilcoxon, F.(1949). J. Pharmacol. exp. Ther., 96, 99–113

Results

Compounds of this invention dosed by the oral route as a suspension in methyl cellulose and tested one hour post dosing showed an increase in seizure threshold. For example, at a dose of 10 mg/kg p.o. the compound of Example 1 showed an increase of 177%, the compound of Example 2 showed an increase of 97%, and the compound of Example 5 showed an increase of 106%.

What is claimed is:

1. A compound of formula (I) or pharmaceutically acceptable salt thereof:

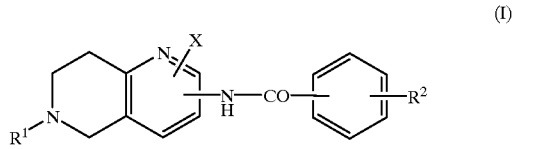

where
$R^1$ is hydrogen, $C_{1-6}$ alkyl optionally substituted by hydroxy or $C_{1-4}$alkoxy, or $C_{1-6}$ alkylphenyl;
$R^2$ is hydrogen or up to three substituents selected from halogen, $NO_2$, CN, $N_3$, $C_{1-6}$ alkylO-, $C_{1-6}$ alkylS-, $C_{1-6}$ alkyl, $C_{3-6}$cycloalkyl, $C_{3-6}$cycloalkyl-$C_{1-4}$alkyl-, $C_{1-6}$alkenyl, $C_{1-6}$alkynyl, $CF_3$, $CF_3O$, $CF_3CO$—, $C_{1-6}$alkylCO-, $C_{3-6}$cycloalkylCO-, $C_{3-6}$cycloalkyl-$C_{1-4}$alkylCO-, phenyl, phenoxy, benzyloxy, benzoyl, phenyl-$C_{1-4}$alkyl-, or —$NR^3R^4$ where
$R^3$ is hydrogen or $C_{1-4}$ alkyl, and
$R^4$ is hydrogen, $C_{1-4}$alkyl, —CHO, —$CO_2C_{1-4}$alkyl or —$COC_{1-4}$alkyl;
or two $R^2$ groups form a saturated carbocyclic ring optionally interrupted by oxygen;
and X is selected from hydrogen, halogen, cyano, alkyl and alkoxy.

2. A compound according to claim 1, selected from the group consisting of:

N-(6-methyl-5,6,7,8-tetrahydro[1,6]naphthyridin-3-yl)-3-bromo-4-methoxybenzamide and its monohydrochloride N-(6-methyl-5,6,7,8-tetrahydro[1,6]naphthyridin-3-yl)-benzamide N-(6-methyl-5,6,7,8-tetrahydro[1,6]naphthyridin-3-yl)-2-methoxy-4-t-butylbenzamide and its monohydrochloride N-(6-methyl-5,6,7,8-tetrahydro[1,6]naphthyridin-3-yl)-4-iso-propoxybenzamide and its monohydrochloride N-(6-methyl-5,6,7,8-tetrahydro[1,6]naphthyridin-3-yl)-4-ethoxybenzamide and its monohydrochloride N-(6-methyl-5,6,7,8-tetrahydro[1,6]naphthyridin-3-yl)-2-methoxy-5-pivaloylbenzamide and its monohydrochloride N-(6-methyl-5,6,7,8-tetrahydro[1,6]naphthyridin-3-yl)-3-trifluoromethyl benzamide and its monohydrochloride N-(6-benzyl-5,6,7,8-tetrahydro[1,6]naphthyridin-3-yl)-3-bromo-4-methoxybenzamide N-(6-methyl-5,6,7,8-tetrahydro[1,6]naphthyridin-3-yl)-4-methoxy-3-trifluoromethylbenzamide and its monohydrochloride N-(6-methyl-5,6,7,8-tetrahydro[1,6]naphthyridin-3-yl)-4-t-butylbenzamide and its monohydrochloride N-(6-methyl-5,6,7,8-tetrahydro[1,6]naphthyridin-3-yl)-3-bromo-4-ethoxybenzamide and its monohydrochloride N-(6-methyl-5,6,7,8-tetrahydro[1,6]naphthyridin-3-yl)-3-bromo-4-iso-propyloxybenzamide and its monohydrochloride N-(6-Methyl-5,6,7,8-tetrahydro[1,6]naphthyridin-3-yl)-3-chloro-4-methoxybenzamide, hydrochloride N-(6-Methyl-5,6,7,8-tetrahydro[1,6]naphthyridin-3-yl)-4-ethyl benzamide N-(6-Methyl-5,6,7,8-tetrahydro[1,6]naphthyridin-3-yl)-4-cyclohexylbenzamide N-(6-Methyl-5,6,7,8-tetrahydro[1,6]naphthyridin-3-yl)-4-benzoylbenzamide N-(6-Methyl-5,6,7,8-tetrahydro[1,6]naphthyridin-3-yl)-2,3-dihydrobenzofuran-5-ylcarboxamide N-(6-Methyl-5,6,7,8-tetrahydro[1,6]naphthyridin-3-yl)-4-t-butyl-3-trifluoromethylbenzamide N-(6-Methyl-5,6,7,8-tetrahydro[1,6]naphthyridin-3-yl)-4-iso-propylbenzamide, hydrochloride N-(6-Methyl-5,6,7,8-tetrahydro[1,6]naphthyridin-3-yl)-4-ethoxy-3-nitrobenzamide hydrochloride N-(6-Methyl-5,6,7,8-tetrahydro[1,6]naphthyridin-3-yl)-3-bromo-4-t-butylbenzamide, hydrochloride N-(6-Methyl-5,6,7,8-tetrahydro[1,6]naphthyridin-3-yl)-3-bromo-4-ethylbenzamide, hydrochloride N-(6-Methyl-5,6,7,8-tetrahydro[1,6]naphthyridin-3-yl)-3-cyano-4-methoxybenzamide, hydrochloride N-(6-Methyl-5,6,7,8-tetrahydro[1,6]naphthyridin-3-yl)-3-bromo-4-n-propyl-oxybenzamide, hydrochloride N-(6-Methyl-5,6,7,8-tetrahydro[1,6]naphthyridin-3-yl)-3,5-dichloro-4-methoxybenzamide, hydrochloride N-(6-Methyl-5,6,7,8-tetrahydro[1,6]naphthyridin-3-yl)-3-bromo-4-iso-propylbenzamide, hydrochloride N-(6-Methyl-5,6,7,8-tetrahydro[1,6]naphthyridin-3-yl)-4-n-propyloxy-3-trifluoromethylbenzamide, hydrochloride N-(6-Methyl-5,6,7,8-tetrahydro[1,6]naphthyridin-3-yl)-3-iodo-4-methoxybenzamide hydrochloride N-(6-Methyl-5,6,7,8-tetrahydro[1,6naphthyridin-3-yl)-4-iso-propyl-3-trifluoromethylbenzamide, hydrochloride N-(6-Methyl-5,6,7,8-tetrahydro[1,6]naphthyridin-3-yl)-3-cyano-4-n-propyloxybenzamide, hydrochloride N-(6-Methyl-5,6,7,8-tetrahydro[1,6]naphthyridin-3-yl)-3-cyano-4-ethoxybenzamide, hydrochloride N-(6-Methyl-5,6,7,8-tetrahydro[1,6]naphthyridin-3-yl)-3-chloro-4-ethoxybenzamide, hydrochloride N-(6-Methyl-5,6,7,8-tetrahydro[1,6]naphthyridin-3-yl)-3-chloro-4-iso-propyloxybenzamide, hydrochloride N-(6-Methyl-5,6,7,8-tetrahydro[1,6]naphthyridin-3-yl)-3-fluoro-4-methoxybenzamide, hydrochloride N-(6-Methyl-5,6,7,8-tetrahydro[1,6]naphthyridin-3-yl]-4-ethyl-3-trifluoromethylbenzamide N-(6-Methyl-5,6,7,8-tetrahydro[1,6]naphthyridin-3-yl)-4-iso-propyloxy-3-trifluoromethylbenzamide, hydrochloride N-(6-Methyl-5,6,7,8-tetrahydro[1,6]naphthyridin-3-yl)-3-iodo-4-methylbenzamide hydrochloride N-(6-Methyl-5,6,7,8-tetrahydro[1,6]naphthyridin-3-yl)-4-azido-3-iodo-benzamide N-(2-Bromo-6-methyl-5,6,7,8-tetrahydro[1,6]naphthyridin-3-yl)-3-bromo-4-ethoxybenzamide N-(2-Bromo-6-methyl-5,6,7,8-tetrahydro[1,6]naphthyridin-3-yl)-4-methoxy-3-trifluoromethylbenzamide, hydrochloride N-(2,6-Dimethyl-5,6,7,8-tetrahydro[1,6]naphthyridin-3-yl)-3-bromo-4-ethoxy-benzamide N-(2,6-Dimethyl-5,6,7,8-tetrahydro[1,6]naphthyridin-3-yl)-4-methoxy-3-trifluoromethylbenzamide N-(2-Cyano-6-methyl-5,6,7,8-tetrahydro[1,6]naphthyridin-3-yl)-4-methoxy-3-trifluoromethylbenzamide N-(2-Chloro-6-methyl-5,6,7,8-tetrahydro[1,6]naphthyridin-3-yl)-3-bromo-4-ethoxybenzamide N-(2-Chloro-6-methyl-5,6,7,8-tetrahydro[1,6]naphthyridin-3-yl)-4-methoxy-3-trifluoromethylbenzamide.

3. A pharmaceutical composition for use in the treatment or prophylaxis of a disorder treatable or preventable with an anti-convulsive agent, migraine, neuralgia, trigeminal neuralgia, neuropathic pain, which comprises a compound according to claim 1 or a pharmaceutically acceptable salt or solvate thereof, and a pharmaceutically acceptable carrier.

4. A method of treatment or prophylaxis of a disorder treatable or preventable with an anti-convulsive agent, migraine, neuralgia, trigeminal neuralgia, neuropathic pain, comprising administering to the sufferer in need thereof an effective or prophylactic amount of a compound according to claim 1 or a pharmaceutically acceptable salt or solvate thereof.

5. A process for the preparation of a compound according to claim 1, which comprises reacting a compound of formula (II)

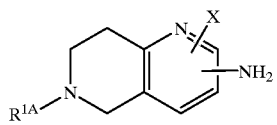

(II)

where $R^{1A}$ is $R^1$ as defined for formula (I) of claim 1 or a group convertible to $R^1$ and X is as defined for formula (I) of claim 1
with a compound of formula (III)

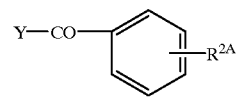

(III)

where Y is Cl or OH, and $R^{2A}$ is $R^2$ as defined for formula (I) or a group or groups convertible to $R^2$, and where required converting a $R^{1A}$ or $R^{2A}$ group to a $R^1$ or $R^2$ group, converting one X, $R^1$ or $R^2$ group to another X, $R^1$ or $R^2$ group, converting a salt product to the free base or another pharmaceutically acceptable salt, or converting a free base product to a pharmaceutically acceptable salt.

6. A pharmaceutical composition for use in the treatment or prophylaxis of a disorder treatable or preventable with an anti-convulsive agent, migraine, neuralgia, trigeminal neuralgia, neuropathic pain, which comprises a compound according to claim 2 or a pharmaceutically acceptable salt or solvate thereof, and a pharmaceutically acceptable carrier.

7. A method of treatment or prophylaxis of a disorder treatable or preventable with an anti-convulsive agent, migraine, neuralgia, trigeminal neuralgia, neuropathic pain, comprising administering to the sufferer in need thereof an effective or prophylactic amount of a compound according to claim 2 or a pharmaceutically acceptable salt or solvate thereof.

* * * * *